United States Patent
Öckerman

(10) Patent No.: US 11,963,992 B2
(45) Date of Patent: Apr. 23, 2024

(54) MULTI-NUTRIENT SUPPLEMENT COMPOSITION AND USES THEREOF

(71) Applicant: Scandinavian Good Business AB, Stockholm (SE)

(72) Inventor: Per-Arne Öckerman, Bohus-Bjorko (SE)

(73) Assignee: Scandinavian Good Business AB, Stockholm (SE)

( * ) Notice: Subject to any disclaimer, the term of this patent is extended or adjusted under 35 U.S.C. 154(b) by 14 days.

(21) Appl. No.: 17/379,255

(22) Filed: Jul. 19, 2021

(65) Prior Publication Data

US 2022/0008498 A1 Jan. 13, 2022

Related U.S. Application Data

(62) Division of application No. 16/389,326, filed on Apr. 19, 2019, now Pat. No. 11,590,190, which is a
(Continued)

(51) Int. Cl.

| | | |
|---|---|---|
| A61K 31/07 | (2006.01) |
| A23L 33/105 | (2016.01) |
| A23L 33/115 | (2016.01) |
| A23L 33/135 | (2016.01) |
| A23L 33/15 | (2016.01) |
| A23L 33/155 | (2016.01) |
| A23L 33/16 | (2016.01) |
| A23L 33/175 | (2016.01) |
| A61K 31/01 | (2006.01) |
| A61K 31/015 | (2006.01) |
| A61K 31/122 | (2006.01) |
| A61K 31/14 | (2006.01) |
| A61K 31/197 | (2006.01) |
| A61K 31/198 | (2006.01) |
| A61K 31/355 | (2006.01) |
| A61K 31/375 | (2006.01) |
| A61K 31/4188 | (2006.01) |
| A61K 31/4415 | (2006.01) |
| A61K 31/455 | (2006.01) |
| A61K 31/51 | (2006.01) |
| A61K 31/519 | (2006.01) |
| A61K 31/525 | (2006.01) |
| A61K 31/59 | (2006.01) |
| A61K 31/593 | (2006.01) |
| A61K 31/7004 | (2006.01) |
| A61K 31/714 | (2006.01) |
| A61K 33/06 | (2006.01) |
| A61K 33/14 | (2006.01) |
| A61K 33/18 | (2006.01) |
| A61K 33/24 | (2019.01) |
| A61K 33/30 | (2006.01) |
| A61K 33/32 | (2006.01) |
| A61K 33/34 | (2006.01) |
| A61K 33/42 | (2006.01) |
| A61K 35/60 | (2006.01) |
| A61K 35/744 | (2015.01) |
| A61K 35/747 | (2015.01) |

(Continued)

(52) U.S. Cl.
CPC .......... *A61K 36/752* (2013.01); *A23L 33/105* (2016.08); *A23L 33/115* (2016.08); *A23L 33/135* (2016.08); *A23L 33/15* (2016.08); *A23L 33/155* (2016.08); *A23L 33/16* (2016.08); *A23L 33/175* (2016.08); *A61K 31/01* (2013.01); *A61K 31/015* (2013.01); *A61K 31/07* (2013.01); *A61K 31/122* (2013.01); *A61K 31/14* (2013.01); *A61K 31/197* (2013.01); *A61K 31/198* (2013.01); *A61K 31/355* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/59* (2013.01); *A61K 31/593* (2013.01); *A61K 31/7004* (2013.01); *A61K 31/714* (2013.01); *A61K 33/06* (2013.01); *A61K 33/14* (2013.01); *A61K 33/18* (2013.01); *A61K 33/24* (2013.01); *A61K 33/30* (2013.01); *A61K 33/32* (2013.01); *A61K 33/34* (2013.01); *A61K 33/42* (2013.01); *A61K 35/60* (2013.01); *A61K 35/744* (2013.01); *A61K 35/747* (2013.01); *A61K 36/45* (2013.01); *A23V 2002/00* (2013.01)

(58) Field of Classification Search
CPC . A61K 35/741; A61K 31/714; A61K 2300/00
See application file for complete search history.

(56) References Cited

U.S. PATENT DOCUMENTS

| | | |
|---|---|---|
| 4,326,523 A | 4/1982 | Wofrom et al. |
| 4,740,373 A | 4/1988 | Kesselman et al. |

(Continued)

OTHER PUBLICATIONS

"U.S. Appl. No. 16/389,326, Response filed Apr. 7, 2022 to Non Final Office Action dated Oct. 7, 2021", 10 pgs.

(Continued)

*Primary Examiner* — Robert T. Crow
*Assistant Examiner* — John P Nguyen
(74) *Attorney, Agent, or Firm* — Schwegman Lundberg & Woessner, P.A.

(57) ABSTRACT

Various embodiments of the invention relate to compositions comprising vitamins, minerals and trace elements, antioxidants, amino acids, probiotics, and other components and methods for using such compositions to treat or prevent diseases associated with oxidative stress, including cardiovascular disease.

4 Claims, No Drawings

Related U.S. Application Data division of application No. 14/104,940, filed on Dec. 12, 2013, now abandoned.

(60) Provisional application No. 61/736,215, filed on Dec. 12, 2012.

(51) Int. Cl.
*A61K 36/45* (2006.01)
*A61K 36/752* (2006.01)

(56) References Cited

U.S. PATENT DOCUMENTS

| | | | |
|---|---|---|---|
| 5,514,382 | A | 5/1996 | Sultenfuss |
| 5,848,443 | A | 12/1998 | Waugh |
| 5,948,443 | A | 9/1999 | Riley et al. |
| 6,048,846 | A | 4/2000 | Cochran |
| 6,299,896 | B1 | 10/2001 | Cooper et al. |
| 7,368,481 | B1 | 5/2008 | Rapisarda |
| 11,590,190 | B2 | 2/2023 | Öckerman |
| 2002/0136711 | A1 | 9/2002 | Cochran |
| 2003/0007961 | A1 | 1/2003 | Wilburn |
| 2004/0001817 | A1 | 1/2004 | Giampapa |
| 2004/0259732 | A1 | 12/2004 | Asrar et al. |
| 2005/0079247 | A1 | 4/2005 | Slilaty |
| 2006/0115555 | A1 | 6/2006 | Foulger et al. |
| 2006/0115556 | A1 | 6/2006 | Foulger et al. |
| 2007/0026108 | A1 | 2/2007 | Foulger |
| 2007/0026109 | A1 | 2/2007 | Foulger |
| 2008/0038367 | A1 | 2/2008 | Saloum |
| 2008/0305096 | A1 | 12/2008 | Verdegem et al. |
| 2010/0291050 | A1 | 11/2010 | Daikeler et al. |
| 2014/0161878 | A1 | 6/2014 | Öckerman |
| 2019/0282647 | A1 | 9/2019 | Öckerman |

OTHER PUBLICATIONS

"U.S. Appl. No. 16/389,326, Final Office Action dated Jul. 29, 2022", 19 pgs.
"U.S. Appl. No. 16/389,326, Response filed Sep. 29, 2022 to Final Office Action dated Jul. 29, 2022", 5 pgs.
"U.S. Appl. No. 16/389,326, Notice of Allowance dated Oct. 28, 2022", 10 pgs.
"", NIH1, [Online]. Retrieved from the Internet: <http://ods.od.nih.gov/pdf/factsheets/VitaminD-HealthProfessional.pdf>, (2014).
"", NIH2, [Online]. Retrieved from the Internet: <http://dietarysupplementdatabase.usda.nih.gov/faq.html>, 2014.
"", ProJoba, [Online]. Retrieved from the Internet: <http://www.youngevity.net/product/PJ520.html>, (2012).
"", Sloan, [Online]. Retrieved from the Internet: <http://www.mskcc.org/cancer-care/herb/quercetin>, 2014.
"", Projoba2, [online]. Retrieved from the Internet: <http://www.youngevity.net/images/pdf/ProJoba/PN7.pdf>, 2014, 1 pgs.
"U.S. Appl. No. 14/104,940, Appeal Brief filed Aug. 29, 2016", 14 pgs.
"U.S. Appl. No. 14/104,940, Appeal Decision dated Feb. 21, 2019", 23 pgs.
"U.S. Appl. No. 14/104,940, Decision on Pre-Appeal Brief Request dated Aug. 31, 2015", 2 pgs.
"U.S. Appl. No. 14/104,940, Examiner's Answer dated Jan. 10, 2017", 23 pgs.
"U.S. Appl. No. 14/104,940, Final Office Action dated Apr. 22, 2015", 22 pgs.
"U.S. Appl. No. 14/104,940, Final Office Action dated Apr. 27, 2016", 20 pgs.
"U.S. Appl. No. 14/104,940, Non Final Office Action dated Oct. 22, 2015", 18 pgs.
"U.S. Appl. No. 14/104,940, Non Final Office Action dated Nov. 17, 2014", 22 pgs.
"U.S. Appl. No. 14/104,940, Pre-Appeal Brief Request filed Jul. 22, 2015", 5 pgs.
"U.S. Appl. No. 14/104,940, Reply Brief filed Mar. 10, 2017", 6 pgs.
"U.S. Appl. No. 14/104,940, Response filed Jan. 22, 2016 to Non Final Office Action dated Oct. 22, 2015", 10 pgs.
"U.S. Appl. No. 14/104,940, Response filed Feb. 17, 2015 to Non Final Office Action dated Nov. 17, 2014", 15 pgs.
"U.S. Appl. No. 16/389,326, Non Final Office Action dated Oct. 7, 2021", 15 pgs.
"U.S. Appl. No. 16/389,326, Preliminary Amendment filed Jun. 12, 2019", 6 pgs.
"U.S. Appl. No. 16/389,326, Response filed Jun. 23, 2021 to Restriction Requirement dated Apr. 2, 2021", 6 pgs.
"U.S. Appl. No. 16/389,326, Restriction Requirement dated Apr. 2, 2021", 6 pgs.
Huys, "", Research in Microbiology 157, (2006), 803-810.
Kimoto, "", Letters in Applied Microbiology, 29, (1999), 313-316.
Kris-Atherton, "", Circulation, 206, (2002), 2747-2757.
Lourens-Hattingh, "", International Dairy Journal 11, (2001), 1-17.
Öckerman, PA, "Improvement of Arterial Stiffness by Multi-Nutrient Supplementation", JOM 26 (4), (2011), 159-162.
Verdenelli, "", Eur J Nutr 48, (2009), 355-363.
U.S. Appl. No. 14/104,940, filed Dec. 12, 2013, Multi-Nutrient Supplement and Uses Thereof.
U.S. Appl. No. 16/389,326, filed Apr. 19, 2019, Multi-Nutrient Supplement and Uses Thereof.

MULTI-NUTRIENT SUPPLEMENT COMPOSITION AND USES THEREOF

CROSS-REFERENCE TO RELATED APPLICATIONS

This application is a divisional of U.S. application Ser. No. 16/389,326, filed Apr. 19, 2019, which is a divisional of U.S. application Ser. No. 14/104,940, filed Dec. 12, 2013, which claims priority under 35 U.S.C. § 119(e) from U.S. Provisional Appl. Ser. No. 61/736,215, filed Dec. 12, 2012, the entirety of all of which is incorporated by reference as if fully set forth herein.

BACKGROUND OF THE INVENTION

Nutritional supplements available today are composed of ingredients that most often act against a particular condition, but not against a spectrum of conditions. For example, probiotics present a popular means for specifically balancing the intestinal flora and food digestion. There are no multi nutritional supplements on the market today, however, that comprise ingredients necessary for, e.g., simultaneously maintaining intestinal flora, supplying beneficial vitamins and trace elements, and combating diseases associated with oxidative stress, including cardiovascular disease (CVD).

SUMMARY OF THE INVENTION

The compositions disclosed herein in various embodiments simultaneously maintain intestinal flora, supply beneficial vitamins and trace elements, and treat or prevent diseases associated with oxidative stress, including cardiovascular disease (CVD). In some embodiments, the compositions disclosed herein delay or prevent the onset of diseases associated with oxidative stress (i.e., primary prevention). In other embodiments, the compositions disclosed herein prevent the progression of diseases associated with oxidative stress by, e.g., relying on early detection of the disease(s) and applying an intervention such as administering a therapeutically effective amount of the compositions disclosed herein (i.e., secondary prevention).

In various embodiments, the invention relates to a method for treating or prevent a disease and/or condition associated with oxidative stress (e.g., CVD) comprising administering to a human subject (e.g., a patient in need thereof) a therapeutically effective amount of a composition comprising vitamin A, vitamin $B_1$, vitamin $B_2$, vitamin $B_3$, vitamin $B_5$, vitamin $B_6$, vitamin $B_{12}$, vitamin C, vitamin D, vitamin E, vitamin K, folic acid, calcium source, potassium source, magnesium source, phosphate source, iodine, copper source, chromium source, manganese source, molybdenum source, selenium source, zinc source, one or more tocopherols or salts thereof, lycopene, one or more carotenoids, one or more flavonoids, biotin, inositol, choline, one or more amino acids, a probiotic composition comprising the powder of one or more dried fruits and pollen extract, and fish oil.

In various other embodiments, the invention relates to a method of delaying or preventing the onset of a disease and/or condition associated with oxidative stress (e.g., CVD) comprising administering to a human subject (e.g., a patient in need thereof) a therapeutically effective amount of a composition comprising vitamin A, vitamin B1, vitamin B2, vitamin B3, vitamin B5, vitamin B6, vitamin B12, vitamin C, vitamin D, vitamin E, vitamin K, folic acid, calcium source, potassium source, magnesium source, phosphate source, iodine, copper source, chromium source, manganese source, molybdenum source, selenium source, zinc source, lycopene, one or more carotenoids, one or more flavonoids, biotin, inositol, choline, one or more amino acids, a probiotic composition comprising the powder of one or more dried fruits and pollen extract, and fish oil.

In still other embodiments, the invention relates to composition comprising:

(i) vitamin A, vitamin $B_1$, vitamin $B_2$, vitamin $B_3$, vitamin $B_5$, vitamin $B_6$, vitamin $B_{12}$, vitamin C, vitamin D, vitamin E, vitamin K, folic acid, calcium source, potassium source, magnesium source, phosphate source, iodine, copper source, chromium source, manganese source, molybdenum source, selenium source, zinc source, lycopene, one or more carotenoids, one or more flavonoids, biotin, inositol, choline, one or more amino acids,
(ii) a probiotic composition comprising the powder of one or more dried fruits and pollen extract,
(iii) fish oil, and
(iv) one or more pharmaceutically acceptable excipients.

DETAILED DESCRIPTION OF THE INVENTION

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "oxidative stress," as used herein broadly refers to biological processes where harmful endogenous or exogenous oxidants, called reactive oxygen species (ROS), causes damage to biological systems and structures. ROS include not only radicals, but other related non-radical species that are formed during intracellular oxidation processes. ROS include, but are not limited to, free radical species, such as superoxide radical anion ($O_2^-$) and hydroxyl radical (—OH); and related non-radical species, such as peroxide (ROOR), hydrogen peroxide ($H_2O_2$), singlet oxygen ($^1O_2$), and peroxynitrite ($ONOO^-$). These free radicals, and related species, participate in the regulation of signal transduction from membrane receptors, immunological and inflammatory responses, smooth muscle relaxation, redox homeostasis, apoptosis, and vascular tone, among others. Proper regulation of ROS provides protection against oxidative stress and provides important mediators in cellular processes. However, excessive production or improper clearance of ROS can result in damage to cellular constituents, such as proteins, DNA, and membrane lipids; dysfunction of intracellular signaling cascades; cytotoxicity; and enzyme inactivation.

Free radicals have been implicated as being important in the pathogenesis in a wide range of diseases and pathological processes, including various forms of cancer, type-2 diabetes mellitus, atherosclerosis, chronic inflammatory conditions, ischemia/reperfusion injury, sepsis, and some neurodegenerative diseases. Droge W., *Physiol. Rev.* 82: 47-95 (2002). Oxidative stress is also thought to be involved in the development of many diseases including Parkinson's disease, Alzheimer's disease, heart failure, myocardial infarction, schizophrenia, bipolar disorder, fragile X syndrome, sickle cell disease, lichen planus, vitiligo, autism, and chronic fatigue syndrome. ROS can also be beneficial, however, as they are used by the immune system as a way to attack and kill pathogens.

Oxidative stress is thought to be linked to certain cardiovascular disease, since oxidation of low-density lipoproteins (LDL) in the vascular endothelium is a precursor to plaque formation. Oxidative stress also plays a role in the ischemic cascade due to oxygen reperfusion injury following hypoxia. This cascade includes both strokes and heart attacks. Oxidative stress has also been implicated in chronic fatigue syndrome. Oxidative stress also contributes to tissue injury following irradiation and hyperoxia, as well as in diabetes.

Oxidative stress is likely to be involved in age-related development of cancer. The reactive species produced in oxidative stress can cause direct damage to DNA and are therefore mutagenic. Oxidative stress can also suppress apoptosis, promote proliferation, invasiveness, and metastasis. Infection by *Helicobacter pylori* which increases the production of reactive oxygen and nitrogen species in human stomach is also thought to be important in the development of gastric cancer.

Oxidative stress is also thought to contribute to the aging process. There is good evidence to support this idea in model organisms such as *Drosophila melanogaster* and *Caenorhabditis elegans*. See, e.g., T. Finkel and N. Holbrook, *Nature* 408: 239-247 (2000).

Embodiments of the present invention are directed to compositions that have been shown to treat or prevent diseases associated with oxidative stress, including cardiovascular disease (CVD; e.g., atherosclerosis, heart infarct, and stroke). These compositions comprise vitamins, minerals and trace elements, antioxidants, amino acids, probiotics, and other components, including biotin, inositol, and choline.

These compositions comprise:
vitamins, in any suitable form, including, but not limited to, at least one of vitamins A (retinyl or salts thereof, such as retinyl acetate), $B_1$ (thiamine or salts thereof, such as thiamine hydrochloride), $B_2$ (riboflavin), $B_3$ (nicotinamide), $B_5$ (calcium-d-pantothenate), $B_6$ (pyridoxine or salts thereof, such as pyridoxine hydrochloride pyridoxine hydrochloride), $B_{12}$ (cyanocobalamine), C, D (cholecalciferol), E (d-alpha-tocopherol acetate, but also beta-, gamma-, and delta-tocopherol or combinations thereof or salts thereof), and K (phylloquinone), and folic acid;

minerals and trace elements, in any suitable form, including, but not limited to, at least one of sources of calcium (e.g., dicalcium phosphate), potassium (e.g., in the form of potassium chloride), magnesium (e.g., in the form of magnesium oxide), phosphorus/phosphate (e.g., in the form of dicalcium phosphate), iodine, copper (e.g., in the form of copper gluconate), chromium (e.g., in the form of chromium sulfate), manganese (e.g., in the form of manganese gluconate), molybdenum (e.g., in the form of potassium molybdate), selenium (e.g. in the form of selenomethionine), and zinc (e.g., zinc lactate);

antioxidants, in any suitable form, including, but not limited to, at least one of tocotrienols or salts thereof, lycopene (e.g., in the form of lycopene extracted from tomatoes), carotenoids (e.g., beta-carotene), flavonoids (e.g., citrus flavonoids from citrus extract any suitable citrus source including, but not limited to orange, lemon, lime, and the like, and including hesperidin, quercetin, rutin, and tangeritin);

amino acids, in any suitable form (e.g., D or L form), including, but not limited to at least one of, arginine (e.g., L-arginine), cysteine (e.g., L-cysteine), and (e.g., N-acetyl cysteine (e.g., N-acetyl-L-cysteine);

probiotics, in any suitable form, including, but not limited to, at least one of a lactic acid bacteria and cultures thereof (e.g., *Lactococcis lactus, Lactobacillus rhamnosus*, cultures thereof and combinations thereof), fructans (e.g., inulin), dried fruit powders (e.g., powder of blueberries), dehydrated fruit or vegetable juice (e.g., beet root juice) or mixtures thereof, and pollen extract from, e.g., Royal Sport Pollen, which comprises pollen extract from *Secale* cereal, *Zea mays*, and *Pinus sylvestris* (available from Allergon AB, Sweden) in a probiotic composition/preparation comprising, e.g., lactic acid bacteria and cultures thereof (e.g., *Lactococcis lactus, Lactobacillus rhamnosus*, cultures thereof and combinations thereof), inulin, and dried powder of blueberries, where the probiotic composition/preparation is in any suitable form including powder form, suspension, emulsion, solution or reconstituted powder, reconstituted with water;

other components, in any suitable form, including, but not limited to, at least one of biotin (e.g., in the form of d-biotin), inositol, choline or salts thereof (e.g., in the form of choline-L-bitartarate), coenzymes (e.g., coenzyme Q10 in isolated form), *Terminalia arjuna* or an extract thereof, including the coenzymes (e.g., coenzyme Q10), glycosides, and tannins present therein; fish oil (e.g. fish oil containing omega-3 fatty acids with 30-80% purity), and vitamers (e.g., compounds that can be converted to the active form of a vitamin).

(e.g., the dosages provided in Table 1 herein) that is sufficient to treat or prevent diseases associated with oxidative stress. These compositions can also be administered over a period of time, with a frequency and duration, sufficient to treat or prevent diseases associated with oxidative stress. In one embodiment, compositions of the present invention comprise the components listed in Table 1 in the amounts shown. It should be understood, however, that those of ordinary skill in the art, with the benefit of the present disclosure, would be able to determine other amounts that would exert the beneficial effects of the compositions of the various embodiments of the present invention.

TABLE 1

| Component | Amount A | Amount B | Amount C | Specific Amounts |
|---|---|---|---|---|
| Vitamin A | 0.01-10 mg | 0.01-10 mg | 0.1-1 mg | 0.4 mg |
| Vitamin $B_1$ | 1-50 mg | 2-30 mg | 1-5 mg | 3.33 mg |
| Vitamin $B_2$ | 1-50 mg | 2-30 mg | 1-5 mg | 3.33 mg |
| Vitamin $B_3$ | 1-100 mg | 5-50 mg | 2-10 mg | 6.67 mg |
| Vitamin $B_5$ | 1-100 mg | 5-50 mg | 2-10 mg | 8 mg |
| Vitamin $B_6$ | 0.5-50 mg | 2-40 mg | 1-5 mg | 4 mg |
| Vitamin $B_{12}$ | 0.0001-2 mg | 0.005-0.05 mg | 0.001-0.01 mg | 0.0067 mg |
| Vitamin C | 0.1-1000 mg | 1-500 mg | 200-500 mg | 413 mg |
| Vitamin D | 0.0001-1 mg | 0.1-1 mg | 0.001-0.01 mg | 0.0033 mg |
| Vitamin E | 1-500 mg | 10-300 mg | 20-50 mg | 33.33 mg |
| Vitamin K | 0.001-5 mg | 0.01-0.5 mg | 0.005-0.05 mg | 0.02 mg |
| Folic Acid | 0.0001-5 mg | 0.005-0.5 mg | 0.01-0.1 mg | 0.067 mg |
| Calcium | 0.1-1000 mg | 100-400 mg | 50-200 mg | 106 mg |
| Potassium | 0.1-1000 mg | 100-800 mg | 50-200 mg | 161 mg |
| Magnesium | 0.1-1000 mg | 50-300 mg | 20-100 mg | 61 mg |
| Phosphorus | 1-500 mg | 100-300 mg | 20-100 mg | 40 mg |
| Iodine | 0.0001-5 mg | 0.001-0.5 mg | 0.005-0.05 mg | 0.01 mg |
| Copper | 0.0001-10 mg | 0.1-3 mg | 0.01-0.5 mg | 0.33 mg |
| Chromium | 0.0001-10 mg | 0.001-1 mg | 0.01-0.5 mg | 0.027 mg |
| Manganese | 0.0001-50 mg | 1-30 mg | 1-5 mg | 3.33 mg |
| Molybdenum | 0.0001-10 mg | 0.001-1 mg | 0.001-0.05 mg | 0.01 mg |
| Selenium | 0.0001-10 mg | 0.001-1 mg | 0.001-0.05 mg | 0.033 mg |
| Zinc | 0.001-50 mg | 1-30 mg | 1-5 mg | 3.33 mg |
| Lycopene | 0.0001-20 mg | 1-15 mg | 1-5 mg | 2 mg |
| Beta-carotene | 0.0001-20 mg | 1-15 mg | 1-5 mg | 2 mg |
| Citrus flavonoids | 1-500 mg | 10-150 mg | 5-50 mg | 16.67 mg |
| Biotin | 0.0001-20 mg | 0.01-1 mg | 0.01-0.5 mg | 0.1 mg |
| Inositol | 0.001-100 mg | 1-30 mg | 1-5 mg | 3.33 mg |
| Choline | 0.0001-500 mg | 10-150 mg | 5-20 mg | 20 mg |
| | 0.0001-20 mg | | | |
| Pollen extract | 1-10,000 mg | 100-5,000 mg | 200-2000 mg | 1000 mg/day |
| L-arginine | 0.0001-100 g | 1-100 g | 1-5 g | 2.25 g/day |
| Fish oil | 0.0001-20 g | 0.01-5 mg | 1-5 g | 2 g/day |
| Probiotics | 1-10 mL | 1-5 mL | 2-8 mL | 5 mL |
| Inulin | 0.0001-100 mg | 0.01-10 mg | 1-20 mg | |
| Blue berries (dried powder) | 0.0001-2000 mg | 0.01-200 mg | 10-500 mg | |

Other lactic acid bacteria include, but are not limited to, *Lactobacillus. acidophilus, L. casei, L. plantarum, L. reuteri, L. helveticus, L. bulgaricus, L. brevis, L. therophilus, Bifidobacterium lactis, B. longum, B. breve, B. bifidum, B. animalis, Lactococcus lactis, Streptococcus thermophilus* and cultures and combinations thereof.

As used herein, the term "in any suitable form" refers broadly to salts, hydrates, clathrates, D/L-forms (e.g., for amino acids); α/β forms (e.g., for polysaccharides), and diastereomers of the vitamins, minerals and trace elements, antioxidants, amino acids, and other components described herein as being present in the compositions of various embodiments of the present invention.

The compositions of the various embodiments of the present invention comprising vitamins, minerals and trace elements, antioxidants, amino acids, probiotics, and other components, can be administered in any suitable dosage It is contemplated that in some embodiments, a range for a component from Amount A might be combined with a range of a different component from Amount B and a range of yet a different component from Amount C. For example, compositions are contemplated herein comprising 0.01-10 mg vitamin A (i.e., the range from Amount A); 2-30 mg vitamin $B_1$ (i.e., the range from Amount B); and 1-5 mg of vitamin $B_2$ (i.e., the range from Amount C).

In some embodiments, the compositions of the various embodiments of the present invention comprising vitamins, minerals and trace elements, antioxidants, amino acids, probiotics, and other components, can comprise elevated levels of vitamin D that are about four-fold the amount given in Table 1. Thus, for example, the amount of vitamin D the compositions of the various embodiments of the present invention comprising vitamins, minerals and trace elements, antioxidants, amino acids, probiotics, and other components, can be about 0.0004 mg to about 4 mg; about 0.4 mg to about 4 mg; about 0.004 mg to about 0.04 mg; or about 0.01 to about 1 mg.

The compositions of the various embodiments of the present invention comprising vitamins, minerals and trace elements, antioxidants, amino acids, probiotics, and other components, may be provided in any suitable form, including tablets, caplets, capsules, tablet-within-a-tablet, tablet/caplet/capsule-within-a-capsule (e.g., Duocap™ available from Capsugel Belgium NV), soft gel capsules, liquid caps (e.g., liquid filled hard capsules), sachets, powders, liquids, and the like.

Some embodiments of the present invention relate to unit dosages, wherein the unit dosages comprises vitamins, minerals and trace elements, antioxidants, amino acids, probiotics, and other components in amounts sufficient to treat or prevent diseases associated with oxidative stress. The term "unit dosage" as used generally herein refers to physically discrete units suitable as unit dosages, each unit comprising vitamins, minerals and trace elements, antioxidants, amino acids, probiotics, and other components in amounts (doses) sufficient to treat or prevent disease and/or condition associated with oxidative stress (e.g., CVD) or in amounts (doses) that are less than the amounts sufficient to treat or prevent a disease and/or condition associated with oxidative stress such that more than one unit dosage is necessary to provide the amounts sufficient to treat or prevent a disease and/or condition associated with oxidative stress. For example, dosage units are contemplated herein where a dosage unit provides 0.01 to 30 doses/dosage unit, e.g., 0.5 to 15 doses/dosage unit; or 1 to 5 doses/dosage unit.

Dosage units include, but are not limited to, tablets, caplets, capsules, tablet-within-a-tablet, tablet/caplet/capsule-within-a-capsule (e.g., Duocap™ available from Capsugel Belgium NV), soft gel capsules, liquid caps (e.g., liquid filled hard capsules) sachets, powders, and the like.

A dosage unit can be, e.g., a single tablet, caplet, capsule, tablet-within-a-tablet, tablet/caplet/capsule-within-a-capsule, soft gel capsules, liquid caps (e.g., liquid filled hard capsules) sachets, powder, and the like, comprising vitamins, minerals and trace elements, antioxidants, amino acids, probiotics, and other components. Alternatively, a dosage unit can comprise two or more tablets, caplets, capsules, tablet-within-a-tablet, tablet/caplet/capsule-within-a-capsule, soft gel capsules, liquid caps (e.g., liquid filled hard capsules) sachets, powder, and the like. For example, a dosage unit can be comprised of a tablet comprising every component but fish oil and probiotics, with the fish oil being in a capsule (or any suitable form), and the probiotics being in a powder (or any suitable form).

In some embodiments, compositions of the present invention comprise vitamins, minerals and trace elements, antioxidants, amino acids, and other components, but lack probiotics and fish oil. Thus, for example, a dosage unit can comprise vitamins, minerals and trace elements, antioxidants, amino acids, and other components, but lack probiotics and fish oil. The probiotics and/or fish oil can be provided separately.

The tablets and caplets contemplated herein may be any suitable tablets and caplets formed using compression methods know in the art, using various pharmaceutically acceptable excipients (e.g., microcrystalline cellulose, isomaltose, magnesium stearate, stearic acid, silicone dioxide, and mannitol). The tablets can also comprise surface treatments including shellac and talcum powder. In some embodiments, a single tablet or caplet can contain the vitamins, minerals and trace elements, antioxidants, amino acids, probiotics, and other components in amounts sufficient to treat or prevent disease and/or condition associated with oxidative stress (e.g., CVD). In various other embodiments, a plurality of tablets or caplets (e.g., two tablets, three tablets, four tablets or more) can contain one or more of the vitamins, minerals and trace elements, antioxidants, amino acids, probiotics, and other components, wherein the plurality of tablets or caplets (or combinations of tablets and caplets), together, comprise vitamins, minerals and trace elements, antioxidants, amino acids, probiotics, and other components in amounts sufficient to treat or prevent disease and/or condition associated with oxidative stress (e.g., CVD).

The compositions of the various embodiments of the present invention comprising vitamins, minerals and trace elements, antioxidants, amino acids, probiotics, and other components, may be administered daily in any suitable interval (e.g., once daily, twice daily, and three times daily). For example, the compositions may be administered one or more time daily such that the daily amounts of the compositions are sufficient to treat or prevent disease and/or condition associated with oxidative stress (e.g., CVD). In some embodiments, 1-5 doses daily are contemplated.

Some embodiments of the present invention relate to a kit comprising a unit dosage, wherein the unit dosage comprises vitamins, minerals and trace elements, antioxidants, amino acids, probiotics, and other components in amounts sufficient to treat or prevent disease and/or condition associated with oxidative stress (e.g., CVD). The kit may comprise one or more suitable containers (e.g., a pouch, plastic bag, box, and the like). In some embodiments, the kit comprises one unit dosage in a suitable container. In other embodiments, the kit comprises more than one unit dosage (e.g., two, five, ten, fifteen, twenty-five, thirty or more unit dosages) in one or more suitable containers.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those of ordinary skill in the art, and that such modifications and variations are considered to be within the scope of this invention as defined by the appended claims.

EXAMPLES

The present invention can be better understood by reference to the following examples which are offered by way of illustration. The present invention is not limited to the examples given herein.

Example 1

A composition (A) was prepared by combining the component listed in Table 2, in the amounts listed, with microcrystalline cellulose, isomaltose, magnesium stearate, stearic acid, silicone dioxide, mannitol. Six tablets can be prepared by compressing composition (A) using tableting techniques known in the art.

TABLE 2

| Component | Preferred Amount |
|---|---|
| Vitamin A | 2.4 mg |
| Vitamin $B_1$ | 20 mg |
| Vitamin $B_2$ | 20 mg |
| Vitamin $B_3$ | 40 mg |
| Vitamin $B_5$ | 48 mg |
| Vitamin $B_6$ | 24 mg |
| Vitamin $B_{12}$ | 0.04 mg |
| Vitamin C | 480 mg |
| Vitamin D | 0.02 mg |
| Vitamin E | 200 mg |
| Vitamin K | 0.12 mg |
| Folic Acid | 0.04 mg |
| Calcium | 320 mg |
| Potassium | 600 mg |
| Magnesium | 200 mg |
| Phosphorus | 240 mg |
| Iodine | 0.06 mg |
| Copper | 2 mg |
| Chromium | 0.16 mg |
| Manganese | 20 mg |
| Molybdenum | 0.06 mg |
| Selenium | 0.2 mg |
| Zinc | 20 mg |
| Lycopene | 12 mg |
| Beta-carotene | 12 mg |
| Citrus flavonoids | 100 mg |
| Biotin | 0.6 mg |
| Inositol | 20 mg |
| Choline | 120 mg |

The specific forms of certain of the component listed in Table 2 is as follows: dicalcium phosphate, potassium chloride, magnesium oxide, copper gluconate, chromium sulfate, manganese gluconate, potassium molybdate, selenomethionine, zinc lactate, extract of tomatoes/lycopene extracted from tomatoes, citrus extract, d-biotin, inositol, and choline-L-bitartarate.

A second composition was prepared that contained elevated vitamin D levels of 0.08 mg and cysteine, but was otherwise identical to composition (A). This second composition, composition (B), was also tableted to provide six tablets.

Compositions (B) was tested using a method identical to the method used to test composition (A). The testing described in this non-limiting example is also described in the Journal of Orthomolecular Medicine 26: 159-162 (2011), the entirety of which is incorporated by reference as if fully set forth herein.

The objective of the tests described in this non-limiting example was to determine if the compositions of various embodiments of the present invention mitigates cardiovascular disease (CVD) risk factors as determined by pulse wave velocity (PWV) and augmentation index (AIX). In the study, the patients were given the compositions described in this non-limiting example.

All patients were thoroughly examined and diagnosed in the ordinary medical system (i.e., the Swedish medical system) before seeking advice from an integrative medicine out-patient clinic where they were routinely tested for aortic arterial stiffness (via measuring PWV) and endothelial function (via measuring AIX) by the arteriography. Patients had many different diagnoses and were on many different types of medications. Smokers and cancer patients were excluded from participating in this study. Selected patients were offered treatment with the compositions of various embodiments of the present invention if their PWV and AIX values indicated that they were at risk of CVD. Patients were considered to be at risk for CVD when their biological age was higher than their actual age, as measured using arteriography by using values from population studies by Illyés M et al.

In total, 85 patients participated, their age ranging from 44-91 years, with a mean age of 67.1 years. A total of 51 females and 34 males completed treatment for two months.

The patients were prescribed the following treatment regimen from eight different containers, each container containing:

1. Composition (A) or (B): 6 tablets/day.
2. Pollen extract: 1000 mg/day from 2 g of granulate.
3. Vitamin C: 2 g/day in tablet form—this is in addition to the vitamin C contained in compositions (A) and (B).
4. L-arginine: 2.25 g/day.
5. N-acetylcysteine: 400 mg/day.
6. Fish oil: 2 g/day comprised of 35% omega-3 essential fatty acids.
7. Minerals, in addition to the minerals contained in compositions (A) or (B): potassium 367 mg/day, magnesium 167 mg/day, and calcium 317 mg/day.
8. Probiotic preparation: 5 mL/day containing *Lactococcis lactus, Lactobacillus rhamnosus*, inulin and dried powder of blueberries.

Assays were made of PWV and AIX using arteriography. Assay values were given as a mean of three measurements at pre-treatment time and after two months of treatment. Values are given for PWV and AIX as determined by the arteriography.

The results shown in Table 3 demonstrate that the compositions of various embodiments of the present invention exert a highly significant effect on PWV and AIX.

TABLE 3

| Parameter Measured | Before Treatment | After Treatment | p-value |
|---|---|---|---|
| PWV (m/s)* | 12.0 | 10.0 | <0.001 |
| PWV (biological age)*/*** | 92.9 | 63.2 | <0.001 |
| AIX*/** | +5.2 | −14.1 | <0.001 |
| Systolic blood pressure (SBP; mm Hg) | 161.4 | 133.0 | <0.001 |
| Diastolic blood pressure (DBP; mm Hg) | 89.6 | 75.2 | <0.001 |
| Central blood pressure (cSBP; mm Hg) | 150.0 | 122.6 | <0.001 |

*Calculated according to *Journal of Orthomolecular Medicine* 26: 159-162 (2011).
**Value calculated from quotient between the pressure peak of the initial and the reflected wave. Percentage of patients that improved: 88.2%
***Calculated according to Illyés, M. et al. Budapest, Hungary.

Table 4 shows the results using the composition (B).

TABLE 4

| Patient No. | PWV biological age before/after treatment (years) | cSBP before/after treatment (mm Hg) |
|---|---|---|
| 1 | 98/76 | 148/132 |
| 2 | 110/90 | 160/152 |
| 3 | 90/78 | 160/142 |
| 4 | 100/90 | 190/142 |
| 5 | 72/56 | 142/140 |
| 6 | 69/44 | 172/169 |
| 7 | 73/27 | 160/123 |

As stated above, the case series involved 85 patients, aged 44-91 years (mean age=67.1 years). The male-to-female distribution was 51 females and 34 males. The compositions (A) or (B) were taken orally during two months. Included were recommended dietary intakes (RDI) of all vitamins, minerals and trace elements, except iron, and higher doses of all B vitamins, vitamin C and E, selenium and magnesium. Other nutrients that were taken orally included L-arginine, fish oil, N-acetylcysteine or cysteine, pollen extract and probiotics.

Measurement of cSBP, AIX, and PWV using artheriography measures the grade of arteriosclerosis and informs about three risk factors for heart infarct and stroke, namely, (i) stiffness in aorta, (ii) the function in smaller arteries, and (iii) central blood pressure. This method is considered to be the "gold standard" by European cardiovascular doctors.

Improvement was seen for PWV in 87.1% and for AIX in 88.2% of patients. Values for AIX decreased from +5.2 to −14.1 and for PWV from 12.0 m/s to 10.0 m/s. The values for PWV can be expressed as a decrease of the biological age of the aorta from 92.9 years to 63.2 years, i.e., a decrease of 29. 7 years (mean decrease in biological age among only the improved patients: 35.8 years). In 85 patients, the compositions of various embodiments of the present invention (e.g., compositions (A) and (B)) produced highly significant improvements in aortic PWV (i.e., aortic artery stiffness) and AIX (i.e., peripheral artery stiffness and function) in two months.

Studies that have evaluated nutrients in the prevention and treatment of CVD used single nutrient interventions. The results of such studies have most often been negative. The background for the approach of the present study was that the compositions of various embodiments of the present invention could afford synergistic effects if the right mix of supplements were used, and therefore prevent negative results due to incipient nutrient deficiencies.

The mechanisms behind the therapeutic effects induced by multiple nutrients are most certainly complex. While not wishing to be bound by any specific theory, it is believed that the addition of essential nutrients, that might be wanting, would help to restore adequate or "healthy" endothelial function. Vitamin C and other antioxidants would counteract oxidation of cholesterol moieties (e.g., low-density lipoprotein cholesterol), but also diminish free radical activity, since oxidative stress is a well-known CVD risk factor. Chronic low-grade inflammation, common to CVD, rheumatoid arthritis and other degenerative diseases, might also be counteracted by judicious nutritional supplementation.

In summary subjects showing elevated levels of the three risk factors showed a decrease in the biological age of aorta with 29.7 years after ingesting the compositions of various embodiments of the present invention for two months. Healthy subjects use the multi nutritional supplement at a lower dose compared to diagnosed subjects for preventing development of atherosclerosis and or other conditions and/or diseases caused by ROS and other environmental factors. The results clearly show a rejuvenation process of the vessels, not only a way of reducing the rate of aging (anti-ageing), but actually a novel and inventive method to return to a lower biological age.

Example 2

The same composition (B) described in Example 1 was prepared in tablet form using standard compression techniques according. Again, six tablets could be prepared from composition (B).

All patients numbering 60 were thoroughly examined and diagnosed in the ordinary medical system (i.e., the Swedish medical system). After analysis using arteriography, patients with abnormal values were offered treatment with composition (A). Smokers and cancer patients were not included. In addition, patients with any other known risk factor for CVD, such as high blood pressure, high lipids, gross overweight, diabetes or rheumatoid arthritis, were also excluded.

Composition (A) was administered for two months using the same treatment regimen as in Example 1. In order to make treatment simpler and less expensive, cysteine was used instead of N-acetyl cysteine, but otherwise in the same amount. Also, it was later found that composition (A) could be combined with pollen extract, vitamin C, L-arginine, N-acetylcysteine, potassium, magnesium, and calcium to make a tablets or capsules that deliver, e.g., 1000 mg/day pollent extract, 2 g/day vitamin C, 2.25 g/day L-arginine, etc. Fish oil and the probiotic were kept separately.

The results from this study are shown in Table 5.

TABLE 5

| Parameter Measured | Before Treatment | After Treatment | p-value |
|---|---|---|---|
| PWV (m/s)* | 11.6 | 9.4 | <0.001 |
| PWV (biological age)*/** | 86.8 | 53.7 | <0.001 |
| AIX*/** | +17.8 | −8.3 | <0.001 |
| SBP (mm Hg) | 154.1 | 136.9 | <0.001 |
| DBP (mm Hg) | 89.4 | 82.3 | <0.001 |
| cSBP (mm Hg) | 161.0 | 136.2 | <0.001 |
| DAI*** | 46.7 | 50.8 | <0.01 |

*Calculated according to Journal of Orthomolecular Medicine 26: 159-162 (2011).
**Calculated according to Illyés, M. et al. Budapest, Hungary.
***Indicative of perfusion of coronary arteries.

Analysis of arterial stiffness and function gives information on several hidden risk factors that may lay behind many cases of sudden and unexpected CVD-events. Thus, a warning can be obtained, leading to treatment and follow-up.

Example 3

The same composition (B) described in Example 1 was prepared in tablet form using standard compression techniques according. Again, six tablets could be prepared from composition (B).

All patients numbering 23 were thoroughly examined and diagnosed in the ordinary medical system (i.e., the Swedish medical system). After analysis using arteriography, patients with abnormal values were offered treatment with composition (A). Smokers and cancer patients were not included.

Composition (A) was administered for two months using the treatment regimen in Example 1. After two months, the regimen was amended to provide fewer composition (A) tablets, less than 1000 mg/day pollen extract, less than 2 g/day additional vitamin C, less than 2.25 g/day L-arginine, less than 400 mg/day N-acetylcysteine, less than 2 g/day fish oil, less than 367 mg/day potassium, less than 167 mg/day magnesium, less than 317 mg/day calcium, and less than 5 mL per day of the probiotic preparation, for an additional 34 months for a total of 36 months of treatment.

The results from this study are shown in Table 6.

TABLE 6

| Parameter Measured | Before Treatment | After Treatment | p-value |
|---|---|---|---|
| PWV (m/s)* | 12.1 | 9.6 | <0.001 |
| PWV (biological age)*/** | 93.3 | 57.0 | <0.001 |
| AIX*/** | +11.5 | −10.1 | <0.001 |

TABLE 6-continued

| Parameter Measured | Before Treatment | After Treatment | p-value |
|---|---|---|---|
| SBP (mm Hg) | 157.2 | 139.0 | <0.001 |
| DBP (mm Hg) | 91.2 | 80.7 | <0.001 |
| cSBP (mm Hg) | 160.5 | 137.1 | <0.001 |
| DAI*** | 49.5 | 52 | <0.01 |

*Calculated according to Journal of Orthomolecular Medicine 26: 159-162 (2011).
**Calculated according to Illyés, M. et al. Budapest, Hungary.
***Indicative of perfusion of coronary arteries.

Analysis of arterial stiffness and function gives information on several hidden risk factors that may lay behind many cases of sudden and unexpected CVD-events. Thus, a warning can be obtained, leading to treatment and follow-up. The results presented may indicate a possibility to diminish several risk factors for CVD and to maintain or even improve further this effect by using lower doses for up to three years.

The present invention provides for the following exemplary embodiments, the numbering of which is not to be construed as designating levels of importance:

Embodiment 1 relates to a method for treating or prevent a disease and/or condition associated with oxidative stress (e.g., CVD) comprising administering to a human subject (e.g., a patient in need thereof) a therapeutically effective amount of a composition comprising vitamin A, vitamin B1, vitamin B2, vitamin B3, vitamin B5, vitamin B6, vitamin B12, vitamin C, vitamin D, vitamin E, vitamin K, folic acid, calcium source, potassium source, magnesium source, phosphate source, iodine, copper source, chromium source, manganese source, molybdenum source, selenium source, zinc source, one or more tocopherols or salts thereof, lycopene, one or more carotenoids, one or more flavonoids, biotin, inositol, choline, one or more amino acids, a probiotic composition comprising the powder of one or more dried fruits and pollen extract, and fish oil.

Embodiment 2 relates to the method of Embodiment 1, wherein the treating comprises preventing the progression of a disease and/or condition associated with oxidative stress.

Embodiment 3 relates to the method of Embodiments 1-2, wherein the disease and/or condition associated with oxidative stress is selected from the group consisting of cardiovascular disease, cancer, type-2 diabetes mellitus, atherosclerosis, chronic inflammatory conditions, ischemia/reperfusion injury, sepsis, neurodegenerative diseases, Parkinson's disease, Alzheimer's disease, heart failure, myocardial infarction, schizophrenia, bipolar disorder, fragile X syndrome, sickle cell disease, lichen planus, vitiligo, autism, chronic fatigue syndrome, and combinations thereof.

Embodiment 4 relates to the method of Embodiment 1-3 wherein the disease and/or condition associated with oxidative stress is cardiovascular disease.

Embodiment 5 relates to the method of Embodiment 4, wherein the cardiovascular disease is at least one of atherosclerosis, heart infarct, and stroke.

Embodiment 6 relates to the method of Embodiments 1-5, wherein the composition comprises vitamin A (0.01-10 mg), vitamin $B_1$ (1-50 mg), vitamin $B_2$ (1-50 mg), vitamin $B_3$ (1-100 mg), vitamin $B_5$ (1-100 mg), vitamin $B_6$ (0.5-50 mg), vitamin $B_{12}$ (0.0001-2 mg), vitamin C (0.1-1000 mg), vitamin D (0.0001-1 mg), vitamin E (1-500 mg), vitamin K (0.001-5 mg), folic acid (0.0001-5 mg), calcium source (0.1-1000 mg), potassium source (0.1-1000 mg), magnesium source (0.1-1000 mg), phosphate source (1-500 mg), iodine source (0.0001-5 mg), copper source (0.0001-10 mg), chromium source (0.0001-10 mg), manganese source (0.0001-50 mg), molybdenum source (0.0001-10 mg), selenium source (0.0001-10 mg), zinc source (0.001-50 mg), lycopene (0.0001-20 mg), one or more carotenoids (0.0001-20 mg), one or more flavonoids (1-500 mg), biotin (0.0001-20 mg), inositol (0.001-100 mg), choline (0.0001-500 mg), one or more amino acids (0.0001-100 g), a probiotic composition (1-10 mL) comprising the powder of one or more dried fruits (0.0001-2000 mg) and pollen extract (1-10,000 mg), and fish oil (0.0001-20 g).

Embodiment 7 relates to the method of Embodiments 1-6, wherein the composition comprises an additional amount of vitamin D such that the total amount of vitamin D is 0.0004-4 mg vitamin D.

Embodiment 8 relates to the method of Embodiments 1-7, wherein the composition comprises an additional amount of at least one of vitamin C, a potassium source, a magnesium source, and a calcium source.

Embodiment 9 relates to the method of Embodiments 1-8, wherein the probiotic composition comprises lactic acid bacteria or cultures thereof (e.g., *Lactococcis lactus* culture, *Lactobacillus rhamnosus* culture, and combinations thereof), inulin, and dried powder of blueberries.

Embodiment 10 relates to the method of Embodiments 1-9, wherein the composition comprises vitamin A, vitamin $B_1$, vitamin $B_2$, vitamin $B_3$, vitamin $B_5$, vitamin $B_6$, vitamin $B_{12}$, vitamin C, vitamin D, vitamin E, vitamin K, folic acid, potassium chloride, magnesium oxide, dicalcium phosphate, iodine, copper gluconate, chromium sulfate, manganese gluconate, potassium molybdate, selenomethionine, zinc lactate, d-alpha-tocopherol acetate, lycopene, beta-carotene, citrus flavonoids, L-cysteine or N-acetyl cysteine, L-arginine, a probiotic composition comprising dried powder of blueberries and pollen extract, d-biotin, inositol, choline-L-bitartarate, and fish oil.

Embodiment 11 relates to a method of delaying or preventing the onset of a disease and/or condition associated with oxidative stress comprising administering to a human subject (e.g., a patient in need thereof) a therapeutically effective amount of a composition comprising vitamin A, vitamin $B_1$, vitamin $B_2$, vitamin $B_3$, vitamin $B_5$, vitamin $B_6$, vitamin $B_{12}$, vitamin C, vitamin D, vitamin E, vitamin K, folic acid, calcium source, potassium source, magnesium source, phosphate source, iodine, copper source, chromium source, manganese source, molybdenum source, selenium source, zinc source, lycopene, one or more carotenoids, one or more flavonoids, biotin, inositol, choline, one or more amino acids, a probiotic composition comprising the powder of one or more dried fruits and pollen extract, and fish oil.

Embodiment 12 relates to a composition comprising:
(i) vitamin A, vitamin $B_1$, vitamin $B_2$, vitamin $B_3$, vitamin $B_5$, vitamin $B_6$, vitamin $B_{12}$, vitamin C, vitamin D, vitamin E, vitamin K, folic acid, calcium source, potassium source, magnesium source, phosphate source, iodine, copper source, chromium source, manganese source, molybdenum source, selenium source, zinc source, lycopene, one or more carotenoids, one or more flavonoids, biotin, inositol, choline, one or more amino acids,
(ii) a probiotic composition comprising the powder of one or more dried fruits and pollen extract,
(iii) fish oil, and
(iv) one or more pharmaceutically acceptable excipients.

Embodiment 13 relates to the composition of Embodiment 12, wherein the composition is in the form of a tablet, powder, liquid, capsule or combinations thereof.

Embodiment 14 relates to the composition of Embodiments 12-13, wherein components (i) and (iv) are comprised in the same dosage unit, separate from the probiotic composition and the fish oil.

Embodiment 15 relates to the composition of Embodiments 12-14, wherein the dosage unit is one or more tablets, caplets, capsules, tablet-within-a-tablet, tablet/caplet/capsule-within-a-capsule, soft gel capsules, liquid caps or sachets.

Embodiment 16 relates to the composition of Embodiments 12-15, wherein the composition comprises vitamin A (0.01-10 mg), vitamin $B_1$ (1-50 mg), vitamin $B_2$ (1-50 mg), vitamin $B_3$ (1-100 mg), vitamin $B_5$ (1-100 mg), vitamin $B_6$ (0.5-50 mg), vitamin $B_{12}$ (0.0001-2 mg), vitamin C (0.1-1000 mg), vitamin D (0.0001-1 mg), vitamin E (1-500 mg), vitamin K (0.001-5 mg), folic acid (0.0001-5 mg), calcium source (0.1-1000 mg), potassium source (0.1-1000 mg), magnesium source (0.1-1000 mg), phosphate source (1-500 mg), iodine source (0.0001-5 mg), copper source (0.0001-10 mg), chromium source (0.0001-10 mg), manganese source (0.0001-50 mg), molybdenum source (0.0001-10 mg), selenium source (0.0001-10 mg), zinc source (0.001-50 mg), lycopene (0.0001-20 mg), one or more carotenoids (0.0001-20 mg), one or more flavonoids (1-500 mg), biotin (0.0001-20 mg), inositol (0.001-100 mg), choline (0.0001-500 mg), one or more amino acids (0.0001-100 g), a probiotic composition (1-10 mL) comprising the powder of one or more dried fruits (0.0001-2000 mg) and pollen extract (1-10,000 mg), and fish oil (0.0001-20 g).

Embodiment 17 relates to the composition of Embodiments 12-16, wherein the composition comprises an additional amount of vitamin D such that the total amount of vitamin D is 0.0004-4 mg vitamin D.

Embodiment 18 relates to the composition of Embodiments 12-17, wherein the composition comprises an additional amount of at least one of vitamin C, a potassium source, a magnesium source, and a calcium source.

Embodiment 19 relates to the composition of Embodiments 12-18, wherein the probiotic composition comprises lactic acid bacteria or cultures thereof (e.g., *Lactococcis lactus* culture, *Lactobacillus rhamnosus* culture, and combinations thereof), inulin, and dried powder of blueberries.

Embodiment 20 relates to the composition of Embodiments 12-19, wherein the composition comprises vitamin A, vitamin $B_1$, vitamin $B_2$, vitamin $B_3$, vitamin $B_5$, vitamin $B_6$, vitamin $B_{12}$, vitamin C, vitamin D, vitamin E, vitamin K, folic acid, potassium chloride, magnesium oxide, dicalcium phosphate, iodine, copper gluconate, chromium sulfate, manganese gluconate, potassium molybdate, selenomethionine, zinc lactate, lycopene, beta-carotene, citrus flavonoids, L-cysteine or N-acetyl cysteine, L-arginine, a probiotic composition comprising dried powder of blueberries and pollen extract, d-biotin, inositol, choline-L-bitartarate, and fish oil.

Embodiment 21 relates to a kit comprising the composition of claims 13-20 in a suitable container.

Embodiment 22 relates to the kit of Embodiment 21, wherein the composition is comprised in a dosage unit.

Embodiment 23 relates to the kit of Embodiment 22, wherein the dosage unit is one or more tablets, caplets, capsules, tablet-within-a-tablet, tablet/caplet/capsule-within-a-capsule, soft gel capsules, liquid caps or sachets.

Embodiment 24 relates to the kit of Embodiments 21-23, wherein the composition comprises vitamin A, vitamin $B_1$, vitamin $B_2$, vitamin $B_3$, vitamin $B_5$, vitamin $B_6$, vitamin $B_{12}$, vitamin C, vitamin D, vitamin E, vitamin K, folic acid, potassium chloride, magnesium oxide, dicalcium phosphate, iodine, copper gluconate, chromium sulfate, manganese gluconate, potassium molybdate, selenomethionine, zinc lactate, lycopene, beta-carotene, citrus flavonoids, L-cysteine or N-acetyl cysteine, L-arginine, a probiotic composition comprising dried powder of blueberries and pollen extract, d-biotin, inositol, choline-L-bitartarate, and fish oil in amounts sufficient to treat or prevent a disease and/or condition associated with oxidative stress.

What is claimed is:

1. A method of delaying or preventing the onset of a disease and/or condition associated with oxidative stress comprising administering to a human subject a therapeutically effective amount of a composition consisting of the following components:
   (i) vitamin A, vitamin B1, vitamin B2, vitamin B3, vitamin B5, vitamin B6, vitamin B12, vitamin C, vitamin D, vitamin E, vitamin K, folic acid, calcium source, potassium source, magnesium source, phosphate source, iodine, copper source, chromium source, manganese source, molybdenum source, selenium source, zinc source, lycopene, one or more carotenoids, one or more flavonoids, biotin, inositol, choline, and one or more amino acids,
   (ii) a probiotic composition comprising at least one of (a) the powder of one or more dried fruits; (b) pollen extract; (c) *Terminalia arjuna* or an extract thereof; (d) at least one lactic acid bacterium or a culture thereof; (e) inulin; and (f) dried powder of blueberries,
   (iii) fish oil, and
   (iv) one or more pharmaceutically acceptable excipients; wherein the composition delays or prevents the onset of a disease and/or condition associated with oxidative stress.

2. The method of claim 1, wherein the at least one lactic acid bacterium comprises *Lactococcis lactus, Lactobacillus rhamnosus*, or cultures and combinations thereof.

3. The method of claim 1, wherein the amounts of component (i)-(iii) are 0.01-10 mg of vitamin A, 1-50 mg of vitamin $B_1$, 1-50 mg of vitamin $B_2$, 1-100 mg of vitamin $B_3$, 1-100 mg of vitamin $B_5$, 0.5-50 mg of vitamin $B_6$, 0.0001-2 mg of vitamin $B_{12}$, 0.1-1000 mg of vitamin C, 0.0001-4 mg of vitamin D, 1-500 mg of vitamin E, 0.001-5 mg of vitamin K, 0.0001-5 mg of folic acid, 0.1-1000 mg of calcium source, 0.1-1000 mg of potassium source, 0.1-1000 mg of magnesium source, 1-500 mg of phosphate source, 0.0001-5 mg of iodine source, 0.0001-10 mg of copper source, 0.0001-10 mg of chromium source, 0.0001-50 mg of manganese source, 0.0001-10 mg of molybdenum source, 0.0001-10 mg of selenium source, 0.001-50 mg of zinc source, 0.0001-20 mg of lycopene, 0.0001-20 mg of one or more carotenoids, 1-500 mg of one or more flavonoids, 0.0001-20 mg of biotin, 0.001-100 mg of inositol, 0.0001-500 mg of choline, 0.0001-100 mg of one or more amino acids, 0.0001-20 g of fish oil and 1-10 mL of the probiotic composition consisting of at least one of 0.0001-2000 mg of the powder of one or more dried fruits and 1-10,000 mg of pollen extract.

4. The method of claim 1, wherein components (i)-(iii) consist of vitamin A, vitamin $B_1$, vitamin $B_2$, vitamin $B_3$, vitamin $B_5$, vitamin $B_6$, vitamin $B_{12}$, vitamin C, vitamin D, vitamin E, vitamin K, folic acid, potassium chloride, magnesium oxide, dicalcium phosphate, iodine, copper gluconate, chromium sulfate, manganese gluconate, potassium molybdate, selenomethionine, zinc lactate, d-alpha-tocopherol acetate, lycopene, beta-carotene, citrus flavonoids, L-cysteine or N-acetyl cysteine, L-arginine, d-biotin, inositol, choline-L-bitartarate, fish oil, and the probiotic composition consisting of at least one of dried powder of blueberries and pollen extract.

* * * * *